(12) United States Patent
Fuchs et al.

(10) Patent No.: US 6,683,177 B1
(45) Date of Patent: *Jan. 27, 2004

(54) PROCESS FOR PRODUCING CAPROLACTAM

(75) Inventors: Eberhard Fuchs, Frankenthal (DE); Johann-Peter Melder, Neuhofen (DE); Werner Schnurr, Herxheim (DE); Rolf Fischer, Heidelberg (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 967 days.

(21) Appl. No.: 08/952,208

(22) PCT Filed: May 7, 1996

(86) PCT No.: PCT/EP96/01892

§ 371 (c)(1),
(2), (4) Date: Nov. 6, 1997

(87) PCT Pub. No.: WO96/36601

PCT Pub. Date: Nov. 21, 1996

(30) Foreign Application Priority Data

May 18, 1995 (DE) .......................... 195 17 823

(51) Int. Cl.$^7$ ..................... C07D 201/08; C07D 223/10
(52) U.S. Cl. ........................ 540/532; 540/539
(58) Field of Search ................. 540/539, 532

(56) References Cited

U.S. PATENT DOCUMENTS

| | | | |
|---|---|---|---|
| 2,208,598 A | 7/1940 | Rigby et al. | 260/464 |
| 2,301,964 A * | 11/1942 | Martin | 260/239 |
| 2,357,484 A * | 9/1944 | Martin | 260/239 |
| 4,012,418 A | 3/1977 | Schaafsma et al. | 260/326 |
| 4,016,175 A * | 4/1977 | Schaafsma et al. | 260/326.62 |
| 4,628,085 A * | 12/1986 | Mares et al. | 540/539 |
| 5,151,543 A | 9/1992 | Ziemecki | 558/459 |
| 5,162,567 A | 11/1992 | Sieja | 558/452 |
| 5,493,021 A * | 2/1996 | Barratt et al. | 540/539 |
| 5,495,016 A * | 2/1996 | Achhammer et al. | 540/539 |
| 5,496,941 A * | 3/1996 | Ritz et al. | 540/540 |
| 5,646,277 A * | 7/1997 | Fuchs et al. | 540/539 |
| 5,693,793 A * | 12/1997 | Ritz et al. | 540/539 |
| 5,739,324 A | 4/1998 | Fuchs et al. | 540/539 |

FOREIGN PATENT DOCUMENTS

| | | |
|---|---|---|
| DE | 749469 | 5/1943 |
| DE | 836 938 | 7/1949 |
| DE | 848 654 | 7/1949 |
| EP | 150295 | 8/1985 |
| EP | 497333 | 8/1992 |
| EP | 502439 | 9/1992 |

OTHER PUBLICATIONS

Official Gazette, 1134 OG 198, Jan. 7, 1992.*
CRC Handbook of Chemistry and Physics, 71$^{st}$ Ed. 3–273, 3–29.

* cited by examiner

Primary Examiner—Bruck Kifle
(74) Attorney, Agent, or Firm—Keil & Weinkauf

(57) ABSTRACT

A process for preparing caprolactam by reacting 6-aminocapronitrile with water in the presence of catalysts comprises using a starting mixture of 6-aminocapronitrile and the tetrahydroazepine derivative of the formula

I

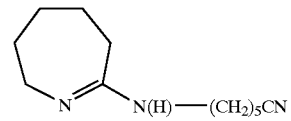

and conducting the reaction in liquid phase in the presence of a heterogeneous catalyst. Also describes a process for preparing said tetrahydroazepine derivative I and its use for preparing caprolactam and polycaprolactam.

8 Claims, No Drawings

PROCESS FOR PRODUCING CAPROLACTAM

The present invention relates to an improved process for preparing caprolactam by reacting 6-aminocapronitrile with water in the presence of catalysts.

On heating or storage at room temperature, 6-aminocapronitrile forms a brown tetrahydroazepine derivative (THA derivative I) of the formula

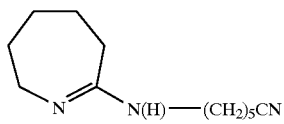

I

THA derivative I shall also encompass its tautomeric form

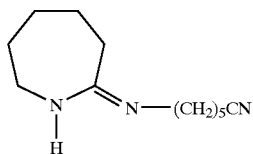

EP-A-497,333 describes the direct polymerization of polycaprolactam starting from 6-aminocapronitrile. The problem to be solved in the process mentioned was the removal of tetrahydroazepine ("THA") before the polymerization step, since tetrahydroazepine leads to discoloration of the polymer obtained on polymerizing caprolactam in the presence of tetrahydroazepine. EP-A-497,333 proposes solving the problem by means of a treatment with a basic compound such as an alkali metal hydroxide or an alkali metal alkoxide. Following the treatment, 6-aminocapronitrile can be conveniently separated from the reaction mixture by distillation, which is not possible without such a treatment. EP-A 502,439 solves the problem of removing THA in the presence of 6-aminocapronitrile by treatment with sodium borohydride. Here too 6-aminocapronitrile can be readily separated from the reaction mixture by distillation after the treatment.

DE-B-25 42 396 and DE-B-25 42 397 describe the conversion of gamma-aminobutyronitrile into a mixture comprising 2-(N-gamma-cyanopropyl)amino-deltal-pyrroline ("CAP") and 2-amino-deltal-pyrroline ("AP"), and also the further hydrolysis of the isolated CAP to 2-pyrrolidone in the absence of catalysts. Neither reference indicates whether the corresponding THA derivative I can be converted into caprolactam in a similar manner in liquid phase in the presence of heterogeneous catalysts. Furthermore, in the cited DE references CAP is first isolated as a pure substance before it is hydrolyzed. It might therefore be expected that the use of mixtures comprising THA derivative I would promote the formation of undesirable by-products. It is also known that five-membered rings are easier to form than seven-membered rings (see Römpp Chemie Lexikon, 9th edition, editors Falbe and Regitz, Georg Thieme verlag, New York). Altogether and on the basis of experience with THA it might therefore be expected that THA derivative I would lead to discolored caprolactam in the cyclization of 6-aminocapronitrile and to discolored polycaprolactam in the direct conversion of 6-aminocapronitrile into polycaprolactam, unless separated off before the cyclization and before the polymerization step.

It might further be expected that THA derivative I would reduce the lifetime of the catalyst used in the polymerization, since it was known from U.S. Pat. No. 5,162,567 that heating THA produces high boilers, ie. compounds or mixtures with a higher boiling point than 6-aminocapronitrile (accordingly making it easy to remove the 6-aminocapronitrile). High boilers, however, tend to form polymeric or oligomeric decomposition products which can form deposits on catalyst surfaces and so reduce not only the lifetime but also the activity of the catalysts.

It is an object of the present invention to provide a process for cyclizing 6-aminocapronitrile to caprolactam wherein THA derivative I reduces neither the lifetime nor the activity of the cyclization catalyst, nor leads to a caprolactam-containing reaction mixture whose UV number is equal to or higher than that prior to the cyclization step. Preferably the post-cyclization UV number should be smaller than pre-cyclization as a function of the pre-cyclization THA derivative I content. Furthermore, any THA derivative I present in the reaction mixture for the direct polymerization of 6-aminocapronitrile shall be easy to remove or it shall be possible to conduct the reaction in such a way that THA derivative I is eliminated.

We have found that this object is achieved by a process for preparing caprolactam by reacting 6-aminocapronitrile with water in the presence of catalysts, which comprises using a starting mixture of 6-aminocapronitrile and the tetrahydroazepine derivative of the formula

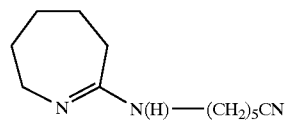

I and conducting the reaction in liquid phase in the presence of a heterogeneous catalyst.

The present invention also provides tetrahydroazepine derivative I, a process for its preparation, and the use of THA derivative I for preparing caprolactam.

The reaction of the present invention is carried out in liquid phase in the presence of heterogeneous catalysts at temperatures from generally 140 to 320 °C., preferably from 160 to 280° C.; the pressure is generally within the range from 41 to 250 bar, preferably from 5 to 150 bar, care having to be taken to ensure that, under the conditions employed, the reaction mixture is predominantly (ie. without the catalyst, which is present in solid phase) liquid. The residence times are generally within the range from 1 to 120, preferably from 1 to 90, in particular from 1 to 60, min. In some cases residence times from 1 to 10 min will prove completely adequate.

The amount of water used is generally at least 0.01 mol, preferably from 0.1 to 20 mol, in particular from 1 to 5 mol, per mole of THA derivative I.

Advantageously THA derivative I is used in the form of a from 1 to 50% strength by weight, in particular from 5 to 50% strength by weight, particularly preferably from 5 to 30% strength by weight, solution in water (in which case the solvent is then also the reactant) or in water-solvent mixtures. Examples of suitable solvents are alkanols such as methanol, ethanol, n- and i-propanol, n-, i- and t-butanol and polyols such as diethylene glycol and tetraethylene glycol, hydrocarbons such as petroleum ether, benzene, toluene, xylene, lactams such as pyrrolidone or caprolactam or alkyl-substituted lactams such as N-methylpyrrolidone, N-methylcaprolactam or N-ethylcaprolactam and also carboxylic esters, preferably of carboxylic acids having from 1 to 8 carbon atoms. Ammonia too can be present in the reaction. It is of course also possible to use mixtures of organic solvents. Mixtures of water and alkanols in a water:alkanol weight ratio of 1–75:25–99, preferably 1–50:50–99, have been determined to be particularly advantageous in some cases.

The THA derivative I content in the 6-aminocapronitrile of the starting mixture can be within the range from 0.01 to 95% by weight, in particular from 0.1 to 50% by weight, particularly preferably from 0.5 to 20% by weight.

The starting mixture customarily has, depending on the level of THA derivative I, a UV number (sum of all absorbances of a 10% by weight solution in ethanol at wavelengths from 280 to 400 nm, based on a path length of 5 cm) within the range from 5 to 40,000.

The starting mixture is obtainable by heating 6-aminocapronitrile with or without solvent. From experience to date, the temperature can be within the range from 20 to 280° C., in particular within the range from 50 to 250° C., particularly preferably within the range from 100 to 230° C. The reaction times are customarily within the range from 10 minutes to 20 hours. As expected, shorter reaction times are possible at higher temperatures. The reaction can be carried out at pressures within the range from 100 kPa to 25 MPa, preferably from 500 kPa to 20 MPa. It can further be advantageous to carry out the reaction in the presence of acidic homogeneous or heterogeneous catalysts such as mineral acid, carboxylic acids, sulfonic acids, titanium dioxide, aluminum oxide, acid ion exchangers or Lewis acids.

If desired, pure THA derivative I can be obtained for example by distillation of unconverted 6-aminocapronitrile, solvents and any by-products.

Examples of suitable heterogeneous catalysts include: acidic, basic or amphoteric oxides of the elements of the second, third or fourth main group of the periodic table, such as calcium oxide, magnesium oxide, boron oxide, aluminum oxide, tin oxide or silicon dioxide as pyrogenic silica, as silica gel, diatomaceous earth, quartz or mixtures thereof, also oxides of metals of secondary groups two to six of the periodic table, such as titanium oxide, amorphous, as anatase and/or rutile, zirconium oxide, zinc oxide, manganese oxide or mixtures thereof. It is also possible to use oxides of the lanthanides and actinides, such as cerium oxide, thorium oxide, praseodymium oxide, samarium oxide, rare earth mixed oxide, or mixtures thereof with the aforementioned oxides. Further catalysts can be, for example:
vanadium oxide, niobium oxide, iron oxide, chromium oxide, molybdenum oxide, tungsten oxide or mixtures thereof. Mixtures between the oxides mentioned are also possible. It is also possible to use sulfides, selenides and tellurides such as zinc telluride, tin selenide, molybdenum sulfide, tungsten sulfide, sulfides of nickel, of zinc and of chromium.

The aforementioned compounds may be doped, ie. contain, compounds of main groups 1 and 7 of the periodic table.

Also suitable are zeolites, phosphates and heteropolyacids and also acidic and alkali iron exchangers such as, for example, Naphion®.

If desired, these catalysts may contain up to 50% by weight each of copper, tin, zinc, manganese, iron, cobalt, nickel, ruthenium, palladium, platinum, silver or rhodium.

The catalysts can be used as solid catalyst or supported catalyst, depending on the composition of the catalyst. For instance, titanium dioxide can be used in the form of a titanium dioxide extrudate or in the form of a thin layer applied to a carrier. Any method described in the literature is suitable for applying $TiO_2$ to a carrier such as silicon dioxide, aluminum oxide or zirconium dioxide. For instance, a thin layer of $TiO_2$ can be applied by hydrolysis of organotitaniums such as titanium isopropoxide or titanium butoxide, or by hydrolysis of $TiCl_4$ or other inorganic Ti-containing compounds. Sols which contain titanium dioxide are also suitable.

Particular preference is given to catalysts which contain no constituents that are soluble under the conditions of the reaction.

In a further preferred embodiment, the reaction is carried out in a fixed bed reactor. A fixed bed process is customarily carried out with tablets or extrudates having diameters within the range from 1 to 10 mm. In principle, however, the reaction can also be carried out in suspension.

In a further preferred embodiment, the reaction is carried out in particular in the presence of a heterogeneous catalyst based on titanium dioxide, zirconium dioxide, cerium oxide or aluminum oxide.

Aluminum oxide is generally suitable in all modifications obtained by heating the precursor compounds aluminum hydroxide (gibbsite, boehmite, pseudoboehmite, bayerite and diaspore) at different temperatures. These include in particular gamma- and alpha-alumina and mixtures thereof.

The oxides can be used in pure form (purity of the respective oxide>80% by weight), as a mixture of the abovementioned oxides, in which case the sum of the abovementioned oxides should be>80% by weight, or as supported catalyst, in which case the abovementioned oxides can be applied to a mechanically and chemically stable carrier usually with a high surface area.

The pure oxides can be prepared by precipitation from aqueous solutions, for example titanium dioxide by the sulfate process or by other processes such as the pyrogenic production of fine alumina, titania or zirconia powders which are commercially available.

Mixtures of various oxides can be prepared in various ways. The oxides or their precursor compounds, which are convertible into the oxides by calcination, can be prepared for example by coprecipitation from solution. This generally brings about very good dispersion of the two oxides used. The oxide or precursor mixtures can also be precipitated by precipitating one oxide or precursor in the presence of a fine suspension of the second oxide or precursor. A further method consists in mechanically mixing the oxide or precursor powders, this mixture can be used as a starting material for producing extrudates or tablets.

Supported catalysts can be prepared by customary methods. For instance, the oxides can be applied to the support by simply impregnating the support with their sols. The sol volatiles are customarily removed from the catalyst by drying and calcining. Sols of this type are commercially available for titania, alumina and zirconia.

A further way of applying layers of the active oxides is the hydrolysis or pyrolysis of organic or inorganic compounds. For instance, a ceramic support can be coated with a thin layer of titanium dioxide by hydrolysis of titanium isopropoxide or other titanium alkoxides. Other suitable compounds include $TiCl_4$, zirconyl chloride, aluminum nitrate and cerium nitrate. Suitable supports are powders, extrudates or tablets of the aforementioned oxides themselves or of other stable oxides such as silica. The supports used can be macroporous to improve the mass transport.

In a further particularly preferred embodiment, the catalyst used is titanium dioxide with an anatase content within the range from 100 to 5, preferably from 99 to 10%, by weight and a rutile content within the range from 0 to 95, preferably from 1 to 90%, by weight, based on the total amount of titanium dioxide. THA derivative I is preferably used for preparing caprolactam by heating it with water/solvent at a temperature within the range from 140 to 320° C., preferably within the range from 160 to 280° C., and a pressure within the range from 100 to 2500, in particular within the range from 500 to 2000, kPa in the presence of the abovementioned heterogeneous catalysts, preferably titania-containing, similarly to the abovementioned starting mixture, using a molar ratio of tetrahydroazepine derivative I to water within the range from 0.01:1 to 20:1, preferably from 0.5:1 to 20:1.

The abovementioned starting mixture as aqueous solution and THA derivative I alone can be directly converted into polycaprolactam by heating by known methods, for example described in EP-A-150,295.

The advantage of the process of the present invention is that it provides a convenient way of processing THA-derivative-I-containing reaction mixtures with 6-aminocapronitrile into caprolactam and, if desired, into polycaprolactam. The products and product mixtures thus obtained are free of troublesome THA derivative I. Thus there is no need for further process steps in the use of additional agents, compared with the removal of THA from corresponding reaction mixtures.

In certain circumstances it can even be advantageous to convert 6-aminocapronitrile in whole or in part into THA derivative I by preheating to temperatures from 20 to 280° C. and to use the resulting mixture of THA derivative I and 6-aminocapronitrile for the cyclization over oxidic catalysts.

EXAMPLES

Example 1

400 g of 6-aminocapronitrile (ACN) were heated to 200° C. for 8 h.

Distillation yielded as second fraction at 0.1 mbar and 140° C. 40 g of THA derivative I (yield 10%) as a pure compound. The characterization was carried out by means of NMR spectroscopy:

$^1$H-NMR (250 MHz, DMSO-d$_6$, TMS, ppm): 4.2 (s, broad, 1 H), 3.2 (m, 2H), 2.9 (t, 2H), 2.45 (t, 2H), 2.25 (m, 2H), 1.7–1.1 (m, 12 H). $^{13}$C-NMR (62.9 MHz, DMSO-d$_6$, TMS, ppm): 163.3 s, 120.6 s, 47.0 t, 41.6 t, 32.9 t, 30.6 t, 29.7 t, 28.4 t, 26.0 t, 25.6 t, 24.8 t, 16.2 t.

Example 2

A 10% by weight ethanolic solution of THA derivative I was pumped together with 2 mol of water (corresponding to 3.2% by weight of the total solution) through a titania-packed tubular reactor (diameter 6 mm; length 800 ml at 70 ml/h. The reactor temperature was 230° C., the pressure was 80 bar. The hourly output was a 9.7% ethanolic caprolactam solution. The solution further obtained 10.8% by weight of recyclable ethyl 6-aminocaproate and also 0.2% by weight of recyclable 6-aminocapronitrile. The caprolactam yield was 80%, the selectivity including the recyclable compounds was 95%.

Example 3

A 10% by weight ethanolic solution consisting of 95% by weight of ACN and 5% by weight of THA derivative I was pumped together with 2 mol of water (corresponding to 3.2% by weight of the total solution) through a titania-packed tubular reactor (diameter 6 mm; length 800 ml at 70 ml/h. The reactor temperature was 230° C., the pressure was 80 bar. The hourly output was a 9.1% ethanolic caprolactam solution. The solution further contained 0.4% by weight of recyclable ethyl 6-aminocaproate and also 0.1% by weight of recyclable 6-aminocapronitrile. The caprolactam yield was 91%, the selectivity including the recyclable compounds was 95%.

Example 4

A 10% by weight ethanolic solution consisting of 99% by weight of ACN and 1% by weight of THA derivative I was pumped together with 2 mol of water (corresponding to 3.2% by weight of the total solution) through a titania-packed tubular reactor (diameter 6 mm; length 800 ml at 70 ml/h. The reactor temperature was 230° C., the pressure was 80 bar. The hourly output was a 9.0% ethanolic caprolactam solution. The solution further contained 0.4% by weight of recyclable ethyl 6-aminocaproate and also 0.1% by weight of recyclable 6-aminocapronitrile. The caprolactam yield was 90%, the selectivity including the recyclable compounds was 95%.

We claim:

1. A process for the preparation of caprolactam by reacting 6-aminocapronitrile with water, which process comprises reacting a mixture of 6-aminocapronitrile and the tetrahydroazepine of the formula (I)

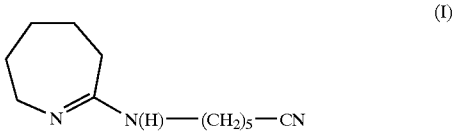

which mixture comprises at least 0.01% by weight of the tetrahydroazepine of the formula I, in the liquid phase in the presence of a heterogeneous catalyst.

2. The process defined in claim 1, which is carried out in a fixed bed reactor.

3. The process defined in claim 1, wherein the heterogeneous catalyst is based on titanium dioxide, zirconium dioxide, cerium oxide or aluminum oxide.

4. The process defined in claim 1, wherein the heterogeneous catalyst comprises of from 5 to 100% by weight of anatase and of from 0 to 95% by weight of rutile, based on the total amount of titanium dioxide.

5. The process defined in claim 1, wherein the mixture of 6-aminocapronitrile and the tetrahydroazepine of the formula (I) has a UV number (sum of all absorbances of a 10% by weight solution in ethanol at wavelengths from 280 to 400 nm, based on a pathlength of 5 cm) within a range from 5 to 40,000.

6. The process defined in claim 1, wherein the mixture of 6-aminocapronitrile and the tetrahydroazepine of the formula (I) comprises of from 0.01 to 95% by weight of 6-aminocapronitrile.

7. The process defined in claim 1, wherein the tetrahydroazepine of the formula (I) is used as a 1 to 50% strength by weight aqueous solution.

8. The process defined in claim 1, which is carried out in the presence of an additional solvent.

* * * * *